United States Patent
Ahnfeldt et al.

(10) Patent No.: US 11,311,464 B2
(45) Date of Patent: Apr. 26, 2022

(54) HAIR CARE BOOSTER IN POWDER FORM AND COSMETIC PRODUCT WITH AN ORGANIC ACID, AND METHOD FOR PREPARATION AND USE THEREOF

(71) Applicant: Henkel AG & Co. KGaA, Duesseldorf (DE)

(72) Inventors: Tina Ahnfeldt, Hamburg (DE); Sylvia Kerl, Boenningstedt (DE); Edith Von Aspern, Hanstedt (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 16/697,985

(22) Filed: Nov. 27, 2019

(65) Prior Publication Data
US 2020/0188239 A1 Jun. 18, 2020

(30) Foreign Application Priority Data
Dec. 18, 2018 (DE) ..................... 10 2018 222 060.3

(51) Int. Cl.
| | | |
|---|---|---|
| *A61K 8/02* | (2006.01) | |
| *A61K 8/19* | (2006.01) | |
| *A61K 8/362* | (2006.01) | |
| *A61K 8/368* | (2006.01) | |
| *A61K 8/44* | (2006.01) | |
| *A61K 8/49* | (2006.01) | |
| *A61K 8/67* | (2006.01) | |
| *A61Q 5/02* | (2006.01) | |

(52) U.S. Cl.
CPC ............... *A61K 8/022* (2013.01); *A61K 8/19* (2013.01); *A61K 8/362* (2013.01); *A61K 8/368* (2013.01); *A61K 8/447* (2013.01); *A61K 8/4953* (2013.01); *A61K 8/676* (2013.01); *A61Q 5/02* (2013.01); *A61K 2800/59* (2013.01)

(58) Field of Classification Search
CPC .......... A61K 8/022; A61K 8/19; A61K 8/362; A61K 8/368; A61K 8/447; A61K 8/4953; A61K 8/676; A61K 2800/59; A61K 2800/882; A61K 8/4946; A61K 8/466; A61K 8/365; A61K 8/44; A61Q 5/02; A61Q 5/12
See application file for complete search history.

(56) References Cited

U.S. PATENT DOCUMENTS

| | | | | |
|---|---|---|---|---|
| 2014/0305462 | A1* | 10/2014 | Knappe | A61Q 5/06 132/203 |
| 2015/0238391 | A1 | 8/2015 | Schoepgens et al. | |
| 2017/0340549 | A1* | 11/2017 | Anderheggen | A61K 8/25 |
| 2018/0042825 | A1* | 2/2018 | Lei | A01N 25/28 |

FOREIGN PATENT DOCUMENTS

| | | |
|---|---|---|
| CN | 108714124 A | 10/2018 |
| DE | 102012220807 A1 | 5/2014 |
| KR | 20130032927 A | 4/2013 |

OTHER PUBLICATIONS

Bauer (EP0401454B1 English Machine Translation) (Year: 1993).*
Anonymous: "Bamboom Volumizing & Cleansing Powder", [Online] www.gnpd.com, Database Accession No. 5621527, XP055668548, Apr. 2018.
Anonymous: "BB Mineral Lucent Powder", [Online] www.gnpd.com, Database Accession No. 4235357, XP055668547, Apr. 2016.
Anonymous: "Facial Washing Powder", [Online] www.gnpd.com, Database Accession No. 3704149, XP055668521, Jan. 2016.
Shaoquing et al.: "UHPLC-TQ-MS Coupled with Multivariate Statistical Analysis to Characterize Nucleosides, Nucleobases and Amino Acids in Angelicae Sinensis Radix Obtained by Different Drying Methods", Molecules Online 2017, 22, 918, pp. 1-15, XP055669356, Jun. 2017.

* cited by examiner

*Primary Examiner* — Quanglong N Truong
(74) *Attorney, Agent, or Firm* — Lorenz & Kopf, LLP

(57) ABSTRACT

A hair care booster in powder form comprises an organic carboxylic acid, a proteinogenic amino acid, a purine or purine degradation products, amino acid degradation products and an alkalizing agent. A cosmetic product comprises the hair care booster in powder form and a separately prepared hair care product. A method comprises mixing the hair care booster in powder form with a hair care product and obtaining a ready-to-use mixture.

20 Claims, No Drawings

HAIR CARE BOOSTER IN POWDER FORM AND COSMETIC PRODUCT WITH AN ORGANIC ACID, AND METHOD FOR PREPARATION AND USE THEREOF

CROSS-REFERENCE TO RELATED APPLICATION

This application claims priority to German Patent Application No. 10 2018 222 060.3, filed Dec. 18, 2018, which is incorporated herein by reference in its entirety.

TECHNICAL FIELD

The technical field relates to hair care products and methods for treating hair, and more particularly relates to a hair care booster in powder form that improves the removal of deposits from hair, a cosmetic product that comprises the hair care booster in powder form, and a method using the hair care booster in powder form.

BACKGROUND

A light, in particular a blonde, hair shade is perceived by many people as beautiful and attractive. However, the light and bright appearance of such a shade can be compromised by a variety of factors, including the deposition and removal and/or ingress of foreign matter, for example from hair care products and/or hair cleansing products. Other sources of deposits on the hair can also play a role; examples are substances which are dissolved or dispersed or in some other form in hair care products or in water such as mains water or swimming pool water, as well as substances which are present in the air, for example as aerosols. On the whole, depending on the individual characteristics of the hair and local environmental conditions, in many cases a somewhat unattractive deposit appears on the hair, and on light hair, in particular light blonde hair, this can trigger a negative visual impression.

Overall, blonde hair needs a great deal of care. Dry ends, yellow tones or loss of color are a few widespread problems which, according to the prevailing opinion, seem to occur more often with blonde hair and with which blonde-haired people constantly have to contend. In addition, many people yearn for a groomed, eye-catching blonde look. This gives rise to a widespread use of lightening and bleaching products, in particular among women, because even in many Western societies, only two percent of all women are naturally light blonde—most blondes have hair which is ash blonde or dark blonde. Thus, bleaching is carried out in order to create what is perceived as the optimal hair color. In bleaching, the cuticle layer of the hair is chemically opened so that the natural color pigments can escape. However, this usually results in brittle and dry hair.

The problem is exacerbated further with increasing hair length, because over a longer timeframe, the hair is subjected to even more of the stresses described above. Thus, consumers with long blonde hair have a particular need for special and particularly good care and cleansing products.

Accordingly, it is desirable to provide a hair care booster to improve the removal of deposits from blonde hair. In addition, it is desirable to provide a method of treating hair using the hair care booster. Furthermore, other desirable features and characteristics will become apparent from the subsequent detailed description and the appended claims, taken in conjunction with the accompanying drawings and the foregoing technical field and background.

BRIEF SUMMARY

Exemplary embodiments of a hair care booster in powder form, a cosmetic product comprising the hair care booster in powder form, and a method using the hair care booster in powered form are provided. In accordance with an exemplary embodiment, a hair care booster in powder form comprises an organic carboxylic acid, a proteinogenic amino acid, a purine or purine degradation products, an amino acid degradation product, and an alkalizing agent.

In accordance with another exemplary embodiment, a cosmetic product is provided. The cosmetic product comprises a hair care booster in powder form and a separately prepared hair care product. The hair care booster in powder form comprises an organic carboxylic acid, a proteinogenic amino acid, a purine or purine degradation products, an amino acid degradation product, and an alkalizing agent.

In accordance with a further exemplary embodiment, a method is provided that comprises mixing a hair care booster in powder form with a hair care product. The hair care booster comprises an organic carboxylic acid, a proteinogenic amino acid, a purine or purine degradation products, an amino acid degradation product, and an alkalizing agent. The method further comprises obtaining a ready-to-use mixture resulting from the mixing.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The various embodiments described herein were developed during the course of research work aimed at addressing the problems outlined above. It concerns a hair care booster, i.e. a product which can be added to a conventional hair care product in order to improve certain of its care and/or cleansing actions in respect of specific parameters, in this case above all the removal of deposits from bleached hair.

The usual way to accomplish this is to recommend special cleansing and care products, such as those which have been developed for hair that has become gray or white, for example, in particular what are known as silver shampoos or special plant-based products to which advantageous effects in this regard have been ascribed. The action of the available products is, however, widely seen as unsatisfactory and consumers are actively exchanging "do-it-yourself" suggestions for improvement. Thus, there is a perceived need for better products for the application described hereinabove.

The underlying aim is therefore to improve the cleansing power of conventional hair care or hair cleansing products, in particular as regards the removal of deposits from blonde hair, in particular from bleached hair. This is achieved in a superlative manner by employing the hair care booster as contemplated herein. In addition, it has been shown that unexpectedly, it can have a positive influence on the internal structure, namely to strengthen that internal structure of treated hair. The underlying aim of the hair care booster is also to improve the internal structure of the hair.

These aims are achieved by a hair care booster in powder form, which comprises an organic carboxylic acid, a proteinogenic amino acid, a purine or purine degradation products, amino acid degradation products and an alkalizing agent, in accordance with an exemplary embodiment. A portioned quantity of this booster is also described as a "shot" or "booster shot" and these terms can be used synonymously. The booster is intended to be added to a conventional hair care product, in particular to a hair treatment, shortly before it is used. In other words, it is an additive or an additive mixture, also termed an additive blend.

There are no particular limitations to the organic carboxylic acid, but in an exemplary embodiment, it is a carboxylic acid containing at most seven, for example, at most six, such as at most four carbon atoms. The organic carboxylic acid may also be a vinylogous carboxylic acid such as ascorbic acid. In an embodiment, the organic carboxylic acid is selected from ascorbic acid, formic acid, malic acid, citric acid, acetic acid, benzoic acid, oxalic acid, maleic acid or a mixture thereof. These carboxylic acids are rather small as regards their molecular size, so that they have good solubilities in water and their carboxylic acid properties compared with larger molecules could be more pronounced over other properties. The advantageous effect of the hair care booster as contemplated herein is particularly pronounced when instigated in this manner.

In an exemplary embodiment, the hair care booster in powder form comprises, with respect to its total weight, from about 50% by weight to about 79% by weight, for example from about 60% by weight to about 74% by weight, such as from about 55% by weight to about 70% by weight of the organic carboxylic acid. It has been shown that a hair care booster in powder form, in which the concentration of the organic carboxylic acids lies in these ranges, exhibits the aforementioned advantageous effects to a greater extent and therefore achieves the underlying aim of the hair care booster in a particularly satisfactory manner. In the hair care booster in powder form, a mixture of different organic carboxylic acids may also be present as the organic carboxylic acid.

In an exemplary embodiment, the hair care booster in powder form comprises, with respect to its total weight, from about 5% by weight to about 15% by weight, for example from about 8% by weight to about 13% by weight, such as from about 9% by weight to about 12% by weight of the proteinogenic amino acid. It has been shown that a hair care booster in powder form, in which the concentration of the proteinogenic amino acid lies in these ranges, exhibits the aforementioned advantageous effects to a greater extent and therefore achieves the underlying aim of the hair care booster in a particularly satisfactory manner. In the hair care booster in powder form, a mixture of different proteinogenic amino acids may also be present as the proteinogenic amino acid.

Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine are proteinogenic amino acids suitable for use in the hair care booster contemplated herein.

In an exemplary embodiment, the hair care booster in powder form comprises, with respect to its total weight, from about 2% by weight to about 10% by weight, for example from about 3% by weight to about 8% by weight, such as from about 4% by weight to about 6% by weight of purine or purine degradation products. It has been shown that a hair care booster in powder form, in which the concentration of the purine or purine degradation products lies in these ranges, exhibits the aforementioned advantageous effects to a greater extent and therefore achieves the underlying aim of the hair care booster in a particularly satisfactory manner. Here again, different purine or purine degradation products in the form of a mixture may be used as the purine or purine degradation products. Specific examples of purine or purine degradation products are adenine, guanine, uric acid, allantoin and hypoxanthine, with which the technically advantageous effect of the hair care booster contemplated herein can be instigated in a particularly pronounced manner.

In another exemplary embodiment, the hair care booster in powder form comprises, with respect to its total weight, 5% by weight to about 15% by weight, for example from about 8% by weight to about 13% by weight, such as from about 9% by weight to about 12% by weight of amino acid degradation products. It has been shown that a hair care booster in powder form, in which the concentration of the amino acid degradation products lies in these ranges, exhibits the aforementioned advantageous effects to a greater extent and therefore achieves the underlying aim of the hair care booster as contemplated herein in a particularly satisfactory manner. The amino acid degradation products may be a specific amino acid degradation product or a mixture of different amino acid degradation products. An exemplary amino acid degradation product is taurine. Amino acid degradation products may also, for their part, still be an amino acid, such as taurine, which is an aminosulfonic acid. Other amino acid degradation products include carboxylic acids or amines. Preferably, the number of carbon atoms in the amino acid degradation product is not too high. In an exemplary embodiment, there are at most six, for example at most five, such as at most four carbon atoms.

In an exemplary embodiment, the hair care booster in powder form preferably comprises, with respect to its total weight, from about 1% by weight to about 8% by weight, for example from about 2% by weight to about 6% by weight, such as from about 3% by weight to about 5% by weight of alkalizing agent. It has been shown that a hair care booster in powder form, in which the concentration of the alkalizing agent lies in these ranges, exhibits the aforementioned advantageous effects to a greater extent and therefore achieves the underlying aim of the hair care booster as contemplated herein in a particularly satisfactory manner.

There are no particular limitations to the alkalizing agent and any alkalizing agent that is acceptable for cosmetic use may be employed. In an exemplary embodiment, the alkalizing agent is an inorganic hydroxide, for example, an alkali or an alkaline earth hydroxide, such as, an alkaline earth hydroxide. In a particular embodiment, the alkalizing agent is calcium hydroxide. It has been shown that by selections of this type, the technically advantageous effects of the hair care booster contemplated herein is achieved to a greater extent.

Another exemplary embodiment contemplated herein provides a cosmetic product that comprises the hair care booster in powder form and a separately prepared hair care product, for example a hair treatment, the use of which achieves the advantages described above. The features described in respect of the hair care booster contemplated herein may also apply to the this embodiment unless specifically contraindicated.

In a further exemplary embodiment, a method is provided that comprises the following steps: mixing the hair care booster in powder form as contemplated herein with a hair care product, for example a hair treatment, and obtaining a ready-to-use mixture. The method, in an embodiment, comprises the step of: using the ready-to-use mixture on keratinous fibers, in particular human hair. The method also may comprise the steps of: leaving the ready-to-use mixture on the keratinous fibers, in particular human hair, for from about 10 seconds to about 20 minutes, and rinsing out the ready-to-use mixture. The step of mixing may be rather short and, in an embodiment, does not exceed four minutes, for example, the time period is in the range from one to three minutes, such as, two minutes. In another embodiment, the period of time between mixing and application to the keratinous fiber is not too long. The period of time between mixing and application to keratinous fibers may, for example, be in the range from about 10 to about 15 minutes.

These exemplary further embodiments mean that the advantageous effects which have already been mentioned are further enhanced, and thus the underlying aims of the hair care booster are achieved in a particularly superlative manner.

The following booster shot composition constitutes a specific exemplary embodiment of the hair care booster contemplated herein:

| Component | Proportion, as a percentage by weight |
|---|---|
| Vitamin C, DAB | 55.60 |
| Citric acid, anhydrous, fine grains | 4.80 |
| Allantoin, USP | 5.30 |
| Lysine HCl | 12.00 |
| Taurine | 12.00 |
| Malic acid, DL | 5.30 |
| Calcium hydroxide | 5.00 |
| Total | 100.00 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair care booster in powder form, consisting of:
an organic carboxylic acid, wherein the organic carboxylic acid is present in an amount of from about 50% by weight to about 79% by weight, based on the total weight of the hair care booster in powder form;
a proteinogenic amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;
a purine or purine degradation product selected from adenine, guanine, uric acid, allantoin and hypoxanthine;
an amino acid degradation product, wherein the amino acid degradation product is taurine; and
an alkalizing agent.

2. The hair care booster in powder form as claimed in claim 1, wherein the organic carboxylic acid is present in an amount of from about 55% by weight to about 74% by weight, based on the total weight of the hair care booster in powder form.

3. The hair care booster in powder form as claimed in claim 1, wherein the organic carboxylic acid is selected from ascorbic acid, formic acid, malic acid, citric acid, acetic acid, benzoic acid, oxalic acid, maleic acid, and a mixture thereof.

4. The hair care booster in powder form as claimed in claim 1, wherein the proteinogenic amino acid is present in an amount of from about 5% by weight to about 15% by weight based on the total weight of the hair care booster in powder form.

5. The hair care booster in powder form as claimed in claim 1, wherein the proteinogenic amino acid is present in an amount of from about 8% by weight to about 13% by weight based on the total weight of the hair care booster in powder form.

6. The hair care booster in powder form as claimed in claim 1, wherein the purine or purine degradation products is present in an amount of from about 2% by weight to about 10% by weight based on the total weight of the hair care booster in powder form.

7. The hair care booster in powder form as claimed in claim 1, wherein the purine or purine degradation product is present in an amount of from about 3% by weight to about 8% by weight based on the total weight of the hair care booster in powder form.

8. The hair care booster in powder form as claimed in claim 1, wherein the amino acid degradation product is present in an amount of from about 5% by weight to about 15% by weight based on the total weight of the hair care booster in powder form.

9. The hair care booster in powder form as claimed in claim 1, wherein the proteinogenic amino acid is present in an amount of from about 9% by weight to about 12% by weight based on the total weight of the hair care booster in powder form.

10. The hair care booster in powder form as claimed in claim 1, wherein the alkalizing agent is present in an amount of from about 1% by weight to about 8% by weight based on the total weight of the hair care booster in powder form.

11. The hair care booster in powder form as claimed in claim 1, wherein the alkalizing agent is an inorganic hydroxide.

12. A cosmetic product comprising:
a hair care booster in powder form as recited in claim 1; and
a separately prepared hair care product.

13. The hair care booster in powder form as claimed in claim 1, wherein the purine or purine degradation products is present in an amount of from about 4% by weight to about 6% by weight based on the total weight of the hair care booster in powder form.

14. The hair care booster in powder form as claimed in claim 1, wherein the amino acid degradation product is present in an amount of from about 8% by weight to about 13% by weight based on the total weight of the hair care booster in powder form.

15. The hair care booster in powder form as claimed in claim 1, wherein the amino acid degradation product is present in an amount of from about 9% by weight to about 12% by weight based on the total weight of the hair care booster in powder form.

16. The hair care booster in powder form as claimed in claim 1, wherein the alkalizing agent is present in an amount of from about 2% by weight to about 6% by weight based on the total weight of the hair care booster in powder form.

17. The hair care booster in powder form as claimed in claim 1, wherein the alkalizing agent is present in an amount of from about 3% by weight to about 5% by weight based on the total weight of the hair care booster in powder form.

18. The hair care booster in powder form as claimed in claim 1, wherein:
- the organic carboxylic acid is present in an amount of from about 55% by weight to about 74% by weight, based on the total weight of the hair care booster in powder form;
- the organic carboxylic acid is selected from ascorbic acid, formic acid, malic acid, citric acid, acetic acid, benzoic acid, oxalic acid, maleic acid, and a mixture thereof;
- the proteinogenic amino acid is present in an amount of from about 9% by weight to about 12% by weight based on the total weight of the hair care booster in powder form;
- the purine or purine degradation product is present in an amount of from about 4% by weight to about 6% by weight based on the total weight of the hair care booster in powder form;
- the amino acid degradation product is present in an amount of from about 9% by weight to about 12% by weight based on the total weight of the hair care booster in powder form;
- the alkalizing agent is present in an amount of from about 3% by weight to about 5% by weight based on the total weight of the hair care booster in powder form; and
- the alkalizing agent is an inorganic hydroxide.

19. The hair care booster in powder form as claimed in claim 18, wherein:
- the organic carboxylic acid is a mixture of ascorbic acid, citric acid, and malic acid;
- the proteinogenic amino acid is lysine;
- the purine or purine degradation product is allantoin;
- the amino acid degradation product is taurine; and
- the alkalizing agent is calcium hydroxide.

20. The hair care booster in powder form as claimed in claim 19, wherein the hair care booster comprises:
- about 55.6 wt. % ascorbic acid;
- about 4.8 wt. % anhydrous Citric acid;
- about 5.3 wt. % Allantoin, USP;
- about 12 wt. % Lysine HCl;
- about 12 wt. % Taurine;
- about 5.30 wt. % Malic acid, DL; and
- about 5.00 wt. % Calcium hydroxide.

\* \* \* \* \*